US010034923B2

(12) United States Patent
Brin

(10) Patent No.: US 10,034,923 B2
(45) Date of Patent: *Jul. 31, 2018

(54) METHODS FOR TREATMENT OF INCONTINENCE ASSOCIATED WITH SEXUAL ACTIVITY

(71) Applicant: Allergan, Inc., Irvine, CA (US)

(72) Inventor: Mitchell F. Brin, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/337,096

(22) Filed: Oct. 28, 2016

(65) Prior Publication Data
US 2017/0042984 A1 Feb. 16, 2017

Related U.S. Application Data

(62) Division of application No. 14/865,547, filed on Sep. 25, 2015, now Pat. No. 9,480,732, which is a division of application No. 13/548,623, filed on Jul. 13, 2012, now Pat. No. 9,144,600.

(60) Provisional application No. 61/507,686, filed on Jul. 14, 2011.

(51) Int. Cl.
*A61K 38/48* (2006.01)
*A61K 9/00* (2006.01)
*A61K 9/08* (2006.01)

(52) U.S. Cl.
CPC ........ *A61K 38/4893* (2013.01); *A61K 9/0019* (2013.01); *A61K 9/0034* (2013.01); *A61K 9/08* (2013.01); *C12Y 304/24069* (2013.01)

(58) Field of Classification Search
None
See application file for complete search history.

(56) References Cited

U.S. PATENT DOCUMENTS

| | | | |
|---|---|---|---|
| 5,437,291 A | 8/1995 | Pasricha et al. | |
| 5,670,484 A | 9/1997 | Binder | |
| 5,714,468 A | 2/1998 | Binder | |
| 5,766,605 A | 6/1998 | Sanders et al. | |
| 6,063,768 A | 5/2000 | First | |
| 6,113,915 A | 9/2000 | Aoki et al. | |
| 6,139,845 A | 10/2000 | Donovan | |
| 6,143,306 A | 11/2000 | Donovan | |
| 6,265,379 B1 | 7/2001 | Donovan | |
| 6,299,893 B1 | 10/2001 | Schwartz et al. | |
| 6,306,403 B1 | 10/2001 | Donovan | |
| 6,306,423 B1 | 10/2001 | Donovan et al. | |
| 6,312,708 B1 | 11/2001 | Donovan | |
| 6,328,977 B1 | 12/2001 | Donovan | |
| 6,358,513 B1 | 3/2002 | Voet et al. | |
| 6,365,164 B1 | 4/2002 | Schmidt | |
| 6,395,277 B1 | 5/2002 | Graham | |
| 6,423,319 B1 | 7/2002 | Brooks et al. | |
| 6,458,365 B1 | 10/2002 | Aoki et al. | |
| 6,464,986 B1 | 10/2002 | Aoki et al. | |
| 7,658,933 B2 | 2/2010 | Foster et al. | |
| 7,659,092 B2 | 2/2010 | Foster et al. | |
| 7,838,007 B2 | 11/2010 | Brin et al. | |
| 7,838,008 B2 | 11/2010 | Brin et al. | |
| 7,846,456 B2 | 12/2010 | Brin et al. | |
| 7,977,335 B2 | 7/2011 | Gil et al. | |
| 8,470,337 B2 | 6/2013 | Manack et al. | |
| 8,501,195 B2 | 8/2013 | Turkel et al. | |
| 8,609,112 B2 | 12/2013 | Blumenfeld et al. | |
| 8,609,113 B2 | 12/2013 | Blumenfeld et al. | |
| 8,889,151 B2 | 11/2014 | Turkel et al. | |
| 8,936,790 B2 | 1/2015 | Turkel et al. | |
| 8,940,308 B2 | 1/2015 | Turkel et al. | |
| 8,968,747 B2 | 3/2015 | Turkel et al. | |
| 9,144,600 B2 * | 9/2015 | Brin .................. | A61K 38/4893 |
| 9,370,548 B2 | 6/2016 | Brin ...................... | A61K 39/08 424/239.1 |
| 9,480,732 B2 * | 11/2016 | Brin .................. | A61K 38/4893 |
| 9,764,011 B2 * | 9/2017 | Turkel .............. | A61K 38/4893 |
| 9,782,547 B2 * | 10/2017 | Hauschild ........ | A61B 17/32037 |
| 2004/0180065 A1 | 9/2004 | Schmidt | |
| 2010/0034802 A1 | 2/2010 | Foster et al. | |
| 2013/0034587 A1 | 2/2013 | Brin | |
| 2015/0374805 A1 * | 12/2015 | Schmidt ................ | A61K 31/16 424/94.67 |
| 2016/0008441 A1 * | 1/2016 | Brin .................. | A61K 38/4893 424/94.67 |
| 2017/0042984 A1 * | 2/2017 | Brin .................. | A61K 38/4893 |

FOREIGN PATENT DOCUMENTS

| | | |
|---|---|---|
| WO | 1999-003483 A1 | 1/1999 |
| WO | 2007-138339 A2 | 12/2007 |
| WO | WO2008030638 | 3/2008 |

(Continued)

OTHER PUBLICATIONS

Abouassaly, R. et al., Ejaculatory Incontinence After Radical Prostatectomy: a Review of 28 Cases, J. Sex. Med., 2005, 14 (Abstracts), 3(1).
Callaway, James et al., Botulinum Toxin Type B: An Overview of Its Biochemistry and Preclinical Pharmacology, Semin Cutan Med Surg. Jun. 2001, 127-136, 20(2).
Fung, Lawrence et al., Pharmacokinetics of Interstitial Delivery of Carmustine, 4-Hydroperoxycyclophosphamide, and Pacitaxel From a Biodegradable Polymer Implant in the Monkey Brain, Cancer Research, Feb. 15, 1998, 672-684, 58.
Habermann, E. et al., 125I-Labeled Neurotoxin from Clostridium Botulinum A:Preparation, Bindingto Synaptosomes and Ascent to the Spinal Cord, 1974, 47-66, 281.
Habermann, Ernst et al., Tetanus Toxin and Botulinum A and C Neurotoxins Inhibit Noradrenaline Release From Cultured Mouse Brian, Journal of Neurochemistry, 1988, 522-527, 51.

(Continued)

*Primary Examiner* — Nita M. Minnifield
(74) *Attorney, Agent, or Firm* — Brigitte C. Phan; Ted A. Chan

(57) ABSTRACT

The invention provides compositions and methods for treating incontinence associated with sexual activity.

17 Claims, No Drawings

(56) References Cited

FOREIGN PATENT DOCUMENTS

| WO | WO2008101098 | 8/2008 |
|---|---|---|
| WO | 2010-138384 A2 | 12/2010 |

OTHER PUBLICATIONS

Marjama-Lyons, Jill et al., Tremor-Predominant Parkinson's Disease: Approaches to Treatment, Drugs & Aging, Apr. 2000, 273-278, 16(4).
Martin, Aaron et al., Incontinence After Radical Prostatectomy: A Patient Centered Analysis and Implications for Preoperative Counseling, Journal of Urology, Jul. 2011, 204-208, 186.
Mitchell, Sarah et al., Post-Prostatectomy Incontinence During Sexual Activity: A Single Center Prevalence Study, Journal of Urology, Sep. 2011, 982-985, 186.
Naumann Markus et al., Botulinum Toxin Type A in the Treatment of Focal, Axiliary and Palmar hyperhidrosis and Other Hyperhidrotic Conditions, European Journal of Neurology, 1999, S111-S115, 6 (4).
Ragona, Rosario Marchese et al., Management of Parotid Sialocele With Botulinum Toxin, Laryngoscope, 1999, 1344-1346, 109(8).
Riss, Paul et al., Quality of Life and Urinary Incontinence in Women, Maturitas, 2011, 137-142, 68.
Sinha, D. et al., Applications of Botulinum Toxin in Urogynaecology, European Journal of Obstetrics & Gynecology and Reproductive Biology, 2007, 4011, 133.
Wiegand, H. et al., 125 I-Labelled Botulinum. A Neurotoxin: Pharmacokinetics in Cats after Intramuscular Injection, Arch Pharmacol, 1976, 161-165, 292.
Patent Cooperation Treaty, Notification of Transmittal of the International Search Report and the Written Opinion of the International Searching Authority, or the Declaration, Form PCT/ISA/220, Int. App. No. PCT/US2012/046720, dated Oct. 10, 2012.
Schimd et al, J. Urology, Jul. 2006, 176/1:177-185.
Hann-Chorng Kuo et al, J. Urology, Nov. 2007, 178(4 Pt 1):1359-1363
Doheny, Kathleen, Sex, Exercise and Stress Incontinence, May 15, 2010, 3 Pages, Retrieved from http://www.webmd.boots.com/sex-relationships/guide/sex-workouts-stress-incontinence?page=3 [retrieved on Sep. 26, 2012].
Hara, Comparison of quality of life following laparoscopic and open prostatectomy for prostate cancer, Journal of Urology, 2003, 2045-2048, 169.
Jae-Chul Lee, Clinical application of Clostridium botulinum type a neurotoxin purified by a simple procedure for patients with urinaqry incontinence caused by refractory destrusor overactivity, FEMS, 2007, 201-211, 51.
Jason Lee, Climacturia following Radical Prostatectomy: Prevalence and risk factors., Journal of Urology, 2006, 2562-2565, 6.
N. Casanova, Botulinum Toxin: A potential alternative to current treatment of neurogenic and idiopathic urinary incontinence due to detrusor overactivity, Surgery and Technology, 2006, 305-311, 95.
Satel, Proceedings from the 14th world meeting of the International Society for Sexual Medicine, Society for Sexual Medicine, 2010, 179-180, Sep. 26-30.
Schurch, Treatment of Neurogenic Incontinence with Botulinum Toxin, New England Journal of Medicine, 2000, 8, n/a.
Sinha, D. et al, Applications of Botulinum Toxin in Urogynaecology, European Journal of Obstetrics & Gynecology and Reproductive Biology, 2007, 4-11, 133.

* cited by examiner

METHODS FOR TREATMENT OF INCONTINENCE ASSOCIATED WITH SEXUAL ACTIVITY

CROSS REFERENCE TO RELATED APPLICATION

This patent application is a Divisional of U.S. patent application Ser. No. 14/865,547, filed Sep. 25, 2015, now U.S. Pat. No. 9,480,732, which is a Divisional of U.S. patent application Ser. No. 13/548,623, filed Jul. 13, 2012, now U.S. Pat. No. 9,144,600, which claims the benefit of U.S. Provisional Patent Application No. 61/507,686, filed Jul. 14, 2011, all of which are hereby incorporated herein by reference in their entirety.

FIELD OF THE INVENTION

The present invention relates to methods for treating incontinence using *botulinum* toxins and other treatments.

BACKGROUND

Incontinence associated with sexual activity encompasses several forms, including orgasm-associated incontinence and climacturia, and can involve incontinence at different points along the sexual spectrum, for example, at penetration, during intercourse, or at climax. The condition can be associated with disorders including overactive bladder (OAB) and neurogenic detrusor overactivity (NDO), and has received increasing attention in the medical literature. Additionally, it can significantly impact sexual satisfaction among both sufferers (both men and women) and their partners. Some male sufferers develop incontinence associated with sexual activity following prostate surgery such as radical prostatectomy (RP; removal of the prostate) or brachytherapy.

Prostate cancer is the second most commonly diagnosed cancer in males in the United States, accounting for approximately 33% of new cancer cases, and is the third leading cause of cancer-related death in men. Several surgery-related complications are associated with RP, including urinary incontinence and sexual dysfunction. The nature and degree of sexual dysfunction can vary widely following RP, including erectile dysfunction, loss of libido, orgasm alterations (anorgasmia, decreased orgasmic intensity, dysorgasmia and orgasm-associated incontinence) and decreased sexual satisfaction. Abouassaly and coworkers (Abouassaly R, Lane B. Lakin M, Klein E, Gill I. Ejaculatory incontinence after radical prostatectomy: a review of 26 cases. Program and abstracts of the Sexual Medicine Society of North America Fall Meeting; Nov. 17-20, 2005; New York, N.Y. Abstract 1) reported their findings with men who had climacturia after having undergone radical prostatectomy. Of an estimated 220 patients evaluated, 26 men experienced urine leak almost exclusively at the time of orgasm. The average age of the patients was 62 years. Patients experienced anywhere from 3 to 120 mL of urine leak (by patient self-report) at the time of orgasm. The authors felt that the occurrence of ejaculatory incontinence is high enough to be considered as part of the routine post-prostatectomy evaluation. In a 2006 study of 42 men, two years following RP, 68% reported experiencing climacturia. Forty-eight percent felt that it was a significant bother to them. In a 2007 study of 475 patients, 20% reported incontinence associated with sexual activity following radical pelvic surgery. Men were more likely to experience it in the first twelve months following surgery than later. Common methods of dealing with incontinence associated with sexual activity include emptying the bladder before sex and wearing a condom during sex. Thus, improved treatment methods are sought.

Men can also display a form of stress incontinence after RP wherein incontinence can occur during intercourse and continue through climax.

In women, incontinence associated with sexual activity may be associated with detrusor overactivity linked to overactive bladder (OAB), or to neurogenic detrusor overactivity (NDO)—one study has found that orgasm can produce an uninhibited detrusor contraction. It has also been associated with female ejaculation in the absence of OAB (Cartwright, 2007) or other urodynamic abnormality. Additionally, some researchers speculate that incontinence associated with sexual activity can be linked with stress or sphincter incontinence. This incontinence can, as in the case with males, occur at any point from before penetration to after climax.

Coital Incontinence (CI) is urinary leakage that occurs during either penetration or orgasm and can occur with a sexual partner or with masturbation. It has been reported to occur in 10% to 24% of sexually active women with pelvic floor disorders, yet CI may still be an underreported problem since sexual or urinary dysfunction may not be often or readily discussed due to patient or physician embarrassment. Unfortunately, CI can have a disturbing impact on Quality of Life (QoL) and sexuality. Women rarely refer to it spontaneously, with only 3% of women self-reporting sexual disorders including CI; even with direct questioning, only 20% will admit to it. The impact on QoL from CI is significant. Sexually active women with CI reported a worse QoL than those without it.

Coital incontinence is divided into 2 subtypes based on when urinary leakage occurs: incontinence with penetration and incontinence with orgasm. Each has different pathophysiologic causes. In the original series of 79 patients with CI, two-thirds experienced CI with penetration, while one-third did so with orgasm. After uro-dynamic testing, CI with penetration was strongly correlated to stress urinary incontinence, while CI from orgasm was strongly correlated with detrusor overactivity. A larger, more recent series of 132 women confirms the findings that the majority of women, 63%, experience CI from penetration, while 37% do so from orgasm.

*Botulinum* toxin type A is the most lethal natural biological agent known to man. About 50 picograms of *botulinum* toxin type A (available from Allergan, Inc., of Irvine, Calif. under the tradename BOTOX®) is an $LD_{50}$ in mice. One unit (U) of *botulinum* toxin is defined as the $LD_{50}$ upon intraperitoneal injection into female Swiss Webster mice weighing 18-20 grams each. Seven immunologically distinct *botulinum* neurotoxins have been characterized, these being respectively *botulinum* neurotoxin serotypes A, B, $C_1$, D, E, F and G, each of which is distinguished by neutralization with type-specific antibodies. The different serotypes of *botulinum* toxin vary in the animal species that they affect and in the severity and duration of the paralysis they evoke. The *botulinum* toxins apparently bind with high affinity to cholinergic motor neurons, are translocated into the neuron and block the release of acetylcholine.

*Botulinum* toxins have been used in clinical settings for the treatment of neuromuscular disorders characterized by hyperactive skeletal muscles. *Botulinum* toxin type A has been approved by the U.S. Food and Drug Administration for the treatment of blepharospasm, strabismus, hemifacial spasm, cervical dystonia, and migraine headaches. *Botuli-*

*num* toxin type B has also been approved by the FDA for the treatment of cervical dystonia. Clinical effects of peripheral intramuscular *botulinum* toxin type A are usually seen within one week of injection. The typical duration of symptomatic relief from a single intramuscular injection of *botulinum* toxin type A averages about three months.

It has been reported that *botulinum* toxin type A has been used in clinical settings as follows:

about 75-125 U (U) of BOTOX® per intramuscular injection (multiple muscles) to treat cervical dystonia;

5-10 U of BOTOX® per intramuscular injection to treat glabellar lines (brow furrows) (5 U injected intramuscularly into the procerus muscle and 10 U injected intramuscularly into each corrugator supercilii muscle);

about 30-80 U of BOTOX® to treat constipation by intrasphincter injection of the puborectalis muscle;

about 1-5 U per muscle of intramuscularly injected BOTOX® to treat blepharospasm by injecting the lateral pre-tarsal orbicularis oculi muscle of the upper lid and the lateral pre-tarsal orbicularis oculi of the lower lid.

to treat strabismus, extraocular muscles have been injected intramuscularly with between about 1-5 U of BOTOX®, the amount injected varying based upon both the size of the muscle to be injected and the extent of muscle paralysis desired (i.e. the amount of diopter correction desired).

to treat upper limb spasticity following stroke by intramuscular injections of BOTOX® into five different upper limb flexor muscles, as follows:

(a) flexor digitorum profundus: 7.5 U to 30 U
(b) flexor digitorum sublimis: 7.5 U to 30 U
(c) flexor carpi ulnaris: 10 U to 40 U
(d) flexor carpi radialis: 15 U to 60 U
(e) biceps brachii: 50 U to 200 U.

Each of the five indicated muscles has been injected at the same treatment session, so that the patient receives from 90 U to 360 U of upper limb flexor muscle BOTOX® by intramuscular injection at each treatment session.

To treat migraine, pericranial (symmetrically into glabellar, frontalis and temporalis muscles) injection of BOTOX® has showed significant benefit as a prophylactic treatment compared to vehicle as measured by decreased measures of migraine frequency, maximal severity, associated vomiting and acute medication use over the three month period following the 25 U injection.

Additionally, intramuscular *botulinum* toxin has been used in the treatment of tremor in patients with Parkinson's disease, although it has been reported that results have not been impressive. Marjama-Jyons, J., et al., Tremor-Predominant Parkinson's Disease, Drugs & Aging 16(4); 273-278: 2000.

In addition to having pharmacologic actions at the peripheral location, *botulinum* toxins may also have inhibitory effects in the central nervous system. Work by Weigand et al., Naunyn-Schmiedeberg's Arch. Pharmacol. 1976; 292, 161-165, and Habermann, Naunyn-Schmiedeberg's Arch. Pharmacol. 1974; 281, 47-56 showed that *botulinum* toxin is able to ascend to the spinal area by retrograde transport.

A *Botulinum* toxin has also been proposed for the treatment of rhinorrhea, hyperhidrosis and other disorders mediated by the autonomic nervous system (U.S. Pat. No. 5,766, 605), tension headache, (U.S. Pat. No. 6,458,365), migraine headache (U.S. Pat. No. 5,714,468), post-operative pain and visceral pain (U.S. Pat. No. 6,464,986), pain treatment by intraspinal toxin administration (U.S. Pat. No. 6,113,915), Parkinson's disease and other diseases with a motor disorder component, by intracranial toxin administration (U.S. Pat. No. 6,306,403), hair growth and hair retention (U.S. Pat. No. 6,299,893), psoriasis and dermatitis (U.S. Pat. No. 5,670, 484), injured muscles (U.S. Pat. No. 6,423,319, various cancers (U.S. Pat. No. 6,139,845), pancreatic disorders (U.S. Pat. No. 6,143,306), smooth muscle disorders (U.S. Pat. No. 5,437,291, including injection of a *botulinum* toxin into the upper and lower esophageal, pyloric and anal sphincters)), prostate disorders (U.S. Pat. No. 6,365,164), inflammation, arthritis and gout (U.S. Pat. No. 6,063,768), juvenile cerebral palsy (U.S. Pat. No. 6,395,277), inner ear disorders (U.S. Pat. No. 6,265,379), thyroid disorders (U.S. Pat. No. 6,358,513), parathyroid disorders (U.S. Pat. No. 6,328,977). Additionally, controlled release toxin implants are known (see e.g. U.S. Pat. Nos. 6,306,423 and 6,312,708).

Adrenergic nerves release norepinephrine as the neurotransmitter for the sympathetic nervous system. The sympathetic system activates and prepares the body for vigorous muscular activity, stress, and emergencies. Adrenergic drugs stimulate the adrenergic nerves directly by mimicking the action of norepinephrine or indirectly by stimulating the release of norepinephrine. An adrenergic agent is a drug, or other substance, which has effects similar to, or the same as, epinephrine (adrenaline). Thus, it is a kind of sympathomimetic agent. Alternatively, it may refer to something which is susceptible to epinephrine, or similar substances, such as a biological receptor (specifically, the adrenergic receptors).

Adrenergic agonists stimulate a response from the adrenergic receptors. The five categories of adrenergic receptors are: $\alpha_1$, $\alpha_2$, $\beta_1$, $\beta_2$, and $\beta_3$, and agonists vary in specificity between these receptors, and may be classified respectively. However, there are also other mechanisms of adrenergic agonism. Epinephrine and norepinephrine are endogenous and broad-spectrum. More selective agonists are more useful in pharmacology.

A great number of drugs are available which can affect adrenergic receptors. Each drug has its own receptor specificity giving it a unique pharmacological effect. Other drugs affect the uptake and storage mechanisms of adrenergic catecholamines, prolonging their action. Agents that work with and activate the adrenergic receptors include alpha- and beta-adrenergic agonists. Agents that increase neurotransmission in endogenous chemicals such as epinephrine and norepinephrine include amphetamines, cocaine, methylenedioxymethamphetamine (MDMA), tyramine, nicotine, caffeine, and methylphenidate. Agents that exhibit aspects of both of these modes include ephedrine and pseudoephedrine.

Adequate treatments for incontinence associated with sexual activity are currently lacking, therefore long-lasting, minimally invasive methods of treatment are desirable.

SUMMARY OF THE INVENTION

Embodiments of the invention include methods of treating incontinence, including urinary incontinence, associated with sexual activity using a *botulinum* toxin. In embodiments the incontinence treatment can comprise treatment of females with climacturia who also have detrusor overactivity, such as, for example, OAB, or NDO, or the like. In embodiments, the OAB or NDO can be state-dependent, i.e. only present at, for example, penetration, or orgasm, or the like. In embodiments the incontinence treatment can comprise treatment of females with climacturia who also have stress incontinence. In certain embodiments the incontinence treatment can comprise treatment of females with climacturia who do not also have demonstrated bladder or outlet disorders. In certain embodiments the incontinence treatment can comprise treatment of males who do not also have demonstrated bladder or outlet disorders. In embodiments the incontinence can occur before, during, or after orgasm. In embodiments the incontinence can occur before, during, or after penetration. In embodiments, the *botulinum* toxin is administered to, for example, the bladder, or the like. In embodiments the toxin is administered, for example, via injection, or transdermally, or via instillation, or the like.

Embodiments include a method of treating post-surgical incontinence associated with sexual activity comprising administering a therapeutically effective amount of a *botulinum* toxin to a patient in need thereof, thereby treating the incontinence associated with sexual activity. In embodiments the incontinence associated with sexual activity occurs following a surgical procedure, such as, for example, for a prostate disorder. In embodiments the surgical procedure is selected from the group consisting of radical prostatectomy, laparoscopic radical prostatectomy, transurethral resection of the prostate, transurethral microwave therapy, transurethral needle ablation, and cryosurgery. In embodiments, the *botulinum* toxin is administered to, for example, the prostate, the bladder, or a combination thereof, or the like. In embodiments the toxin is administered, for example, via injection, or transdermally, or via instillation, such as into the bladder, or the like. In embodiments the incontinence can occur before, during, or after orgasm. In embodiments the incontinence can occur before, during, or after penetration.

Embodiments include a method of preventing post-surgical incontinence associated with sexual activity comprising administering a therapeutically effective amount of a *botulinum* toxin to a patient in need thereof, thereby preventing the incontinence associated with sexual activity. In embodiments the incontinence associated with sexual activity occurs following a surgical procedure, such as, for example, for a prostate disorder. In embodiments the surgical procedure is selected from the group consisting of radical prostatectomy, laparoscopic radical prostatectomy, transurethral resection of the prostate, transurethral microwave therapy, transurethral needle ablation, and cryosurgery. In embodiments, the *botulinum* toxin is administered to, for example, the prostate, the bladder, or a combination thereof, or the like. In embodiments the toxin is administered, for example, via injection, or transdermally, or via instillation, such as into the bladder, or the like. In embodiments the patient is administered the *botulinum* toxin at a time selected from the group consisting of before surgery, during surgery, after surgery, and combinations thereof. In embodiments the incontinence can occur before, during, or after orgasm. In embodiments the incontinence can occur before, during, or after penetration.

In embodiments of the invention the *botulinum* toxin is selected from the group consisting of types A, B, C, D, E, and, G.

Embodiments of the invention include methods of treating incontinence, including urinary incontinence, associated with sexual activity using a *botulinum* toxin in combination with, for example, a drug that has an effect on the tonicity of the bladder or sphincter muscle, such as the urinary sphincter. In embodiments the incontinence treatment can comprise treatment of females with climacturia who also have detrusor overactivity, such as, for example, OAB, or NDO, or the like. In embodiments, the OAB or NDO can be state-dependent, i.e. only present at, for example, penetration, or orgasm, or the like. In embodiments the incontinence treatment can comprise treatment of females with climacturia who also have stress incontinence. In certain embodiments the incontinence treatment can comprise treatment of females with climacturia who do not also have demonstrated bladder or outlet disorders. In certain embodiments the incontinence treatment can comprise treatment of males who do not also have demonstrated bladder or outlet disorders. In embodiments the incontinence can occur before, during, or after orgasm. In embodiments the incontinence can occur before, during, or after penetration. In embodiments, the *botulinum* toxin in combination with a drug that has an effect on the tonicity of a sphincter muscle is administered to, for example, the bladder, or the like. In embodiments the toxin is administered, for example, via injection, or transdermally, or via instillation, or the like.

Embodiments of the invention include methods of treating incontinence, including urinary incontinence, associated with sexual activity using a drug that has an effect on the tonicity of the bladder or sphincter muscle, such as the urinary sphincter. In embodiments the incontinence treatment can comprise treatment of females with climacturia who also have detrusor overactivity, such as, for example, OAB, or NDO, or the like. In embodiments, the OAB or NDO can be state-dependent, i.e. only present at, for example, penetration, or orgasm, or the like. In embodiments the incontinence treatment can comprise treatment of females with climacturia who also have stress incontinence. In certain embodiments the incontinence treatment can comprise treatment of females with climacturia who do not also have demonstrated bladder or outlet disorders. In certain embodiments the incontinence treatment can comprise treatment of males who do not also have demonstrated bladder or outlet disorders. In embodiments the incontinence can occur before, during, or after orgasm. In embodiments the incontinence can occur before, during, or after penetration. In embodiments, the *botulinum* toxin in combination with a drug that has an effect on the tonicity of a sphincter muscle is administered to, for example, the bladder, or the like. In embodiments the toxin is administered, for example, via injection, or transdermally, or via instillation, or the like.

In embodiments the drug that has an effect on the tonicity of the sphincter muscle can be, for example, an anticholinergic, or an adrenergic, such as an alpha- or beta-adrenergic agonist, or amphetamines, cocaine, methylenedioxymethamphetamine (MDMA), tyramine, nicotine, caffeine, and methylphenidate. In embodiments the drug that has an effect on the tonicity of the bladder or sphincter muscle can be any drug that relaxes smooth muscles in the gastrointestinal tract, or relaxes bladder muscles, or increases contraction of the bladder sphincter. For example, SUDAFED® contains the active ingredient pseudoephedrine and refers to a family of over the counter (OTC) decongestants manufactured by McNeil Laboratories (a division of Johnson & Johnson) for sale in Australia, New Zealand, Canada, Ireland, South Africa, the United Kingdom, and the United States. The drug exhibits an anticholinergic effect and thus is suitable for use in embodiments of the invention. Other anticholinergics suitable for use in embodiments of the invention include oxybutynin (Ditropan), tolterodine (Detrol), darifenacin (Enablex), fesoterodine (Toviaz), solifenacin (Vesicare) and trospium (Sanctura).

Other drugs that can be used in embodiments of the present invention include Imipramine and Duloxetine.

DESCRIPTION OF EXEMPLARY EMBODIMENTS

The present invention meets this need and provides for improved methods for treating incontinence associated with sexual activity. In some embodiments, the methods comprise the step of locally administering a neurotoxin (e.g., a *botulinum* toxin type A and/or other types) to at least one anatomical site. In some embodiments, the dose of neurotoxin to be administered is equivalent to about 1 U to about 500 U of a *botulinum* toxin type A. In certain embodiments, the method of administration can be systemic, such as, for example, intravenously, or local, such as, for example, via injection into the prostate or bladder or a combination thereof, by implant, with a topical formulation, via instillation, or the like.

In one aspect, the invention comprises a method of treating incontinence associated with sexual activity in patients who also have detrusor overactivity, such as, for example, OAB, or NDO, or the like, comprising administering an effective amount of a *botulinum* toxin composition to the surface or within the tissue of a patient in need thereof. In certain embodiments, for example, the *botulinum* toxin composition comprises *botulinum* toxin encapsulated in phospholipid micelles, and/or one or more primary stabilizers, and/or one or more skin penetration enhancers. In an example, 50 U, or 75 U, or 100 U, or 150 U, or 200 U, or 300 U, or 400 U of *botulinum* toxin type A is instilled into the bladder of a patient suffering from incontinence associated with sexual activity wherein the patient also suffers from detrusor overactivity. In alternate embodiments, 50 U, or 75 U, or 100 U, or 150 U, or 200 U, or 300 U, or 400 U of *botulinum* toxin type A is injected into the bladder of a patient suffering from incontinence associated with sexual activity wherein the patient also suffers from detrusor overactivity.

In one aspect, the invention comprises a method of treating post-surgical incontinence associated with sexual activity, such as, for example, following RP, comprising administering an effective amount of a *botulinum* toxin composition to the surface or within the tissue of a patient in need thereof. In certain embodiments, for example, the *botulinum* toxin composition comprises *botulinum* toxin encapsulated in phospholipid micelles, and/or one or more primary stabilizers, and/or one or more skin penetration enhancers. In certain embodiments, for example, such treatment can comprise administration of a *botulinum* to toxin to the prostate via, for example, injection, topical administration, or the like.

In one aspect, the invention comprises a method of preventing post-surgical incontinence associated with sexual activity, such as, for example, following RP, comprising administering an effective amount of a *botulinum* toxin composition to the surface or within the tissue of a patient in need thereof. In certain embodiments, for example, the *botulinum* toxin composition comprises *botulinum* toxin encapsulated in phospholipid micelles, and/or one or more primary stabilizers, and/or one or more skin penetration enhancers. In certain embodiments, for example, such treatment can comprise administration of a *botulinum* to toxin to the prostate via, for example, injection, topical administration, or the like.

Definitions

The following definitions apply herein.

"About" means plus or minus ten percent of the value so qualified.

"Alleviating" means a reduction in or prevention of the occurrence of a symptom related to incontinence associated with sexual activity. Thus, alleviating includes some reduction, significant reduction, near total reduction, and total reduction of a symptom related to incontinence associated with sexual activity. An alleviating effect may not appear clinically for between 1 and 7 days after administration of a *botulinum* toxin to a patient.

"*Botulinum* toxin" means a *botulinum* neurotoxin as either pure toxin (i.e. about 150 kDa weight molecule) or as a complex (i.e. about 300 to about 900 kDa weight complex comprising a neurotoxin molecule and one or more associated non-toxic molecules), and excludes *botulinum* toxins which are not neurotoxins such as the cytotoxic *botulinum* toxins C2 and C3, but includes recombinantly made, hybrid, modified, and chimeric *botulinum* toxins.

"Drug that has an effect on the tonicity of the bladder or sphincter muscle" means any drug, compound, or molecule that can affect the muscle tension of the bladder or a sphincter muscle, such as the urinary sphincter.

"Effective amount" as applied to the neurotoxin means that amount of the neurotoxin generally sufficient to effect a desired change in the subject. In some embodiments, the neurotoxin can be administered in an amount between about 0.01 U/kg and about 35 U/kg and the symptoms of the condition can be substantially alleviated for between about 1 month and about 27 months, for example for from about 1 month to about 6 months.

"Improved patient function" means an improvement measured by factors such as reduced pain, reduced time spent in bed, reduced urination upon climax, increased ambulation, healthier attitude, more varied lifestyle and/or healing permitted by normal muscle tone. Improved patient function is synonymous with an improved quality of life (QoL). QoL can be assessed using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

"Incontinence" means the unintended release of bodily fluid, not limited to urine.

"Incontinence associated with sexual activity" means the unintended release of bodily fluid, not limited to urine, during sexual activity.

"Locally administering" or "local administration" means direct administration to a location, such as, for example, by injection, instillation, implant, or topical application, such as, for example, using microemulsion creams or topical compositions. Local administration excludes systemic routes of administration, such as intravenous or oral administration.

"Sexual activity" means any act relating to sex, including, for example, foreplay, penetration, intercourse, oral sex, etc.

"Treating" means to alleviate (or to eliminate) at least one symptom related to climacturia, such as incontinence, either temporarily or permanently.

"Urogenic abnormality" means any condition causing a urologic effect, such as OAB, NDO, stress incontinence, sphincter incontinence, etc.

The pharmaceutical compositions contemplated by this invention include pharmaceutical compositions suited for topical and local action.

In some embodiments the term "topical" as employed herein relates to the use of a composition, as described herein, incorporated in a suitable pharmaceutical carrier. Accordingly, such topical compositions include those pharmaceutical forms in which the compound is applied externally by direct contact with the skin surface to be treated. Conventional pharmaceutical forms for this purpose include ointments, liniments, creams, shampoos, lotions, pastes, jellies, sprays, aerosols, and the like, and can be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these. In some embodiments, the term "topical" as employed herein relates to the use of a composition suitable for instillation, a procedure in which a fluid is introduced into a cavity or passage of the body and allowed to remain for a specific length of time before being drained or withdrawn. It is performed to expose the tissues of the area to the solution, to warmth or cold, or to a drug or substance in the solution. In some embodiments, the composition can be warmed or cooled prior to instillation.

The compositions can be applied a single time or repeatedly at regular or non-regular intervals for a sustained period of time. In certain embodiments, compositions of the invention can be administered topically to the part of the body to be treated. In certain embodiments, compositions of the invention can be administered systemically, such as, for example, intravenously.

For topical use, the compositions can be formulated in aqueous solutions, creams, ointments or oils exhibiting physiologically acceptable osmolarity by addition of pharmacologically acceptable buffers and salts. Such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid etc. as additives. Furthermore, particularly aqueous solutions may contain viscosity increasing agents such as polysaccharides, e.g., methylcellulose, mucopolysaccharides, e.g., hyaluronic acid and chondroitin sulfate, or polyalcohol, e.g., polyvinylalcohol. Various slow releasing gels and matrices may also be employed as well as soluble and insoluble ocular inserts, for instance, based on substances forming in-situ gels. Depending on the actual formulation and compound to be used, various amounts of the drug and different dose regimens may be employed.

The neurotoxins of the instant invention can be administered by any suitable means. In an embodiment of the invention, botulinum toxin is administered by injection. Such injection can be administered to any affected area. For example, the neurotoxin can be injected urethroscopically into the prostate with, for example, 100 U with single or serial dosing, or 200 U with single or serial dosing, or 300 U with single or serial dosing, or 400 U with single or serial dosing, or the like. In certain embodiments, the neurotoxin is injected every three weeks, or every four weeks, or every five weeks, or a lesser or greater interval, or the like until a therapeutic effect is achieved, or up to about 2500 U, or up to about 3000 U, or up to about 3500 U, or more, or the like.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Exemplary, commercially available, botulinum toxin containing compositions include, but are not limited to, BOTOX® (botulinum toxin type A neurotoxin complex with human serum albumin and sodium chloride) available from Allergan, Inc., of Irvine, Calif. in 100 U vials as a lyophilized powder to be reconstituted with 0.9% sodium chloride before use), DYSPORT® (Clostridium botulinum type A toxin haemagglutinin complex with human serum albumin and lactose in the formulation, available from Ipsen Limited, Berkshire, U.K. as a powder to be reconstituted with 0.9% sodium chloride before use) which can be used at about 3 to about 4 times the amounts of BOTOX® as set forth herein in each instance, and MYOBLOC® (an injectable solution comprising botulinum toxin type B, human serum albumin, sodium succinate, and sodium chloride at about pH 5.6, available from Solstice Neurosciences, Inc., South San Francisco, Calif.) which can be used at about 30 to about 50 times the amounts of BOTOX® as set forth herein in each instance, as known in the art. XEOMIN® (a 150 kDa botulinum toxin type A formulation available from Merz Pharmaceuticals, Potsdam, Germany) is another useful neurotoxin which can be used at about 1 to about 2 times the amounts of BOTOX® as set forth herein in each instance.

In additional embodiments, no less than about 10 U and no more about 400 U of BOTOX®; or no less than about 30 U and no more than about 1600 U of DYSPORT®; or no less than about 250 U and no more than about 20000 U of MYOBLOC® are administered per site, per patient treatment session.

In still further embodiments, no less than about 20 U and no more than about 300 U of BOTOX®; or no less than about 60 U and no more than about 1200 U of DYSPORT®; or no less than about 1000 U and no more than about 15000 U of MYOBLOC® are administered per site, per patient treatment session.

Although the composition may only contain a single type of botulinum toxin, such as, for example, type A, as the active ingredient, other therapeutic compositions may include two or more types of botulinum toxins. For example, a composition administered to a patient may include botulinum toxin type A and botulinum toxin type B, or the like. Administering a single composition containing two different neurotoxins can permit the effective concentration of each of the neurotoxins to be lower than if a single neurotoxin is administered to the patient while still achieving the desired therapeutic effects. The composition administered to the patient may also contain other pharmaceutically active ingredients, such as, for example, protein receptor or ion channel modulators, or the like, in combination with the neurotoxin or neurotoxins.

In certain embodiments, compositions of the invention can comprise re-targeted endopeptidases; molecules derived by replacing the naturally-occurring binding domain of a clostridial toxin with a targeting domain showing a selective binding activity for a non-clostridial toxin receptor present in a cell of interest. Such modifications to the binding domain result in a molecule that is able to selectively bind to a non-clostridial toxin receptor present on the target cell. A re-targeted endopeptidase can bind to a target receptor, translocate into the cytoplasm, and exert its proteolytic effect on the SNARE complex of the neuronal or non-neuronal target cell of interest. In certain embodiments of the invention, the composition can comprise re-targeted endopeptidases.

Re-targeted endopeptidases can decrease the effects of sensory afferents, including conditions that are predominantly motor in origin. See, for example, U.S. Pat. No.

7,658,933 to Foster et al., titled "Non-Cytotoxic Protein Conjugates"; U.S. Pat. No. 7,659,092 to Foster et al., titled "Fusion Proteins"; and U.S. Ser. No. 12/303,078 to Foster et al., titled "Treatment of Pain," all incorporated entirely by reference. In addition, endopeptidases can modulate pain associated with multiple medical conditions.

Certain embodiments of the invention can utilize a combination of re-targeted endopeptidases and *botulinum* toxins. The combination of *botulinum* toxins and re-targeted endopeptidases allows for dose reduction of active agents (with associated reduction in side effects) as well as possible synergistic effects. Non-paralytic effects, and also possible prophylactic effects especially when used early in the condition can provide further benefits. The molar ratio of *botulinum* toxin to re-targeted endopeptidases in the combination treatment can be, for example, a 1:1 ratio; a 1:2 ratio; a 1:5 ratio; a 1:10 ratio; a 1:20 ratio; a 1:50 ratio; a 1:100 ratio; 1:200 ratio; a 1:500 ratio; a 1:1000 ratio; 1:2,000 ratio; a 1:5,000 ratio; a 1:10,000 ratio, or the like. In certain embodiments the molar ratio of *botulinum* toxin to re-targeted endopeptidases in the combination treatment can be, for example, a 1:1 ratio; a 2:1 ratio; a 5:1 ratio; a 10:1 ratio; a 20:1 ratio; a 50:1 ratio; a 100:1 ratio; 200:1 ratio; a 500:1 ratio; a 1000:1 ratio; 2000:1 ratio; a 5000:1 ratio; a 10,000:1 ratio, or the like.

Certain embodiments of the invention can utilize an implant for administration. Implants useful in practicing the methods disclosed herein may be prepared by mixing a desired amount of a stabilized *Botulinum* toxin (such as non-reconstituted BOTOX®) or re-targeted endopeptidases into a solution of a suitable polymer dissolved in methylene chloride. The solution can be prepared at room temperature. The solution can then be transferred to a Petri dish and the methylene chloride evaporated in a vacuum desiccator. Depending upon the implant size desired and hence the amount of incorporated neurotoxin or re-targeted endopeptidases, a suitable amount of the dried neurotoxin-incorporating implant is compressed at about 8000 p.s.i. for 5 seconds or at 3000 p.s.i. for 17 seconds in a mold to form implant discs encapsulating the neurotoxin. See e.g. Fung L. K. et al., Pharmacokinetics of Interstitial Delivery of Carmustine 4-Hydroperoxycyclophosphamide and Paclitaxel From a Biodegradable Polymer Implant in the Monkey Brain, Cancer Research 58; 672-684:1998. Embodiments of the invention can also utilize *botulinum* toxins in powder form, and/or administered via a needleless injection system, or the like.

In certain embodiments, administration of the composition can follow, accompany, or precede a surgical procedure, such as, for example, radical prostatectomy, laparoscopic radical prostatectomy, transurethral resection of the prostate, transurethral microwave therapy, transurethral needle ablation, cryosurgery, and the like.

Additionally, in some embodiments, a physician can alter dosage in each case in accordance with the assessment of the severity of the condition, as typically done when treating patients with a condition/disorder. Further, in some embodiments, the treatment may have to be repeated at least one additional time, in some cases several times, depending on the severity of the condition and the patient's overall health. If, for example, a patient is not deemed physically suitable for a full administration of *botulinum* toxin, or if a full administration is not desired for any reason, smaller doses on multiple occasions may prove to be efficacious.

Of course, an ordinarily skilled medical provider can determine the appropriate dose and frequency of administration(s) to achieve an optimum clinical result. That is, one of ordinary skill in medicine would be able to administer the appropriate amount of the toxin, for example *botulinum* toxin type A, at the appropriate time(s) to effectively treat the disorder. The dose of the neurotoxin to be administered depends upon a variety of factors, including the severity of the disorder. The dose of the toxins employed in accordance with this invention may be equivalent to the dose of BOTOX® used in accordance with the present invention described herein. In various methods of the present invention, from about 0.01 U/kg (U of *botulinum* toxin per kilogram of patient weight) to about 15 U/kg, of a BOTOX® e.g. *botulinum* toxin type A, can be administered. In some embodiments, about 0.1 U/kg to about 20 U/kg of BOTOX® may be administered. Use of from about 0.1 U/kg to about 30 U/kg of a BOTOX®, is within the scope of a method practiced according to the present disclosed invention. In one embodiment, about 0.1 U/kg to about 150 U/kg *botulinum* toxin, for example type A, may be administered.

Significantly, a method within the scope of the present invention can provide improved patient function.

The *botulinum* toxin composition can be administered at, for example, a dose of 10 to 1000 U of *botulinum* toxin per affected site, or a dose of 20 to 800 U of *botulinum* toxin per affected site, or a dose of 50 to 500 U of *botulinum* toxin per affected site, or a dose of 100 to 400 U of *botulinum* toxin per affected site, or a dose of 200 to 300 U of *botulinum* toxin per affected site, or the like.

In some embodiments, the affected area can comprise multiple toxin administration sites.

Suitable active ingredients for inclusion in the composition include *botulinum* toxin type A, type B, type C, type D, type E, type F, and type G. Other active ingredients can include, but are not limited to androgens, androstenediol and androisoxazole (for anabolic disorders), testosterone (hypogonadism, muscle wasting, male impotence, postmenopausal symptoms in women), dihydrotestosterone (hypogonadism, muscle wasting), dihydrotestosterone (muscle wasting, fat reduction, fitness); estrogens (postmenopausal symptoms, birth control), 17 betaestradiol, estradiol-3,17-diacetate, estradiol-3-acetate, estradiol-17-acetate, estradiol-3, 17-valerate, estradiol-3-valerate, estradiol-17-valerate, ethinyl estradiol, estrone; progesterones (prevent endometriosis, prevent endometrial cancer, control habitual abortion, suppress or synchronize estrus, promote hair growth), progesterone (preg-4-ene-3,20-dione), norethindrone, norgesterone, norgestrienone, norgestrel, norgestimate, progestogenic acid, dihydroprogesterol, nomegestrol. The testosterone hormone may be used in any of its usual forms, such as, acetate, propionate, 17-beta-cyclopentanepropionate, enanthate, isobutyrate, undecanoate, and the like. Similarly, the estradiols may additionally be used in any of the known or newly developed forms, such as, for example, pivalate, propionate, cypionate, benzoate and other esters.

In certain embodiments, compositions of the invention can include agents that promote healing. For example, vasodilators, such as nitroglycerin and glycerin mononitrate can be encapsulated in a phospholipid micelle and then combined with collagen and/or elastin in a lotion or cream formulation and applied to the skin. Without being limited by the explanation, it is thought that the formulation of vasodilators in the composition enhances the rate of penetration as compared to administration via, for example, a skin patch. Inclusion of hydrogen peroxide and/or a perfluorocarbon may further enhance oxygenation and healing.

The composition can contain a single active ingredient or multiple active ingredients in the same composition. Various combinations of active ingredients are contemplated for inclusion in the composition.

Skin or mucus membrane penetration enhancers that promote the absorption of an active ingredient by the skin or mucus membrane can also be included in the composition. Examples of skin or mucus membrane penetration enhancers include, but are not limited to, alcohols, such as short chain alcohols, long chain alcohols, or polyalcohols, amines and amides, such as urea, amino acids or their esters, amides, AZONE®, derivatives of AZONE®, pyrrolidones, or derivatives of pyrrolidones; terpenes and derivatives of terpenes; fatty acids and their esters; macrocyclic compounds; tensides; or sulfoxides such as, decylmethylsulfoxide. Liposomes, transfersomes, lecithin vesicles, ethosomes, water surfactants, such as anionic, cationic, and nonionic surfactants, polyols, and essential oils can also function as skin or mucus membrane penetration enhancers.

Embodiments of the invention can comprise micelles, such as, for example, phospholipid micelles. In certain embodiments, the phospholipid micelles may comprise sphingosine and cerebroside, for example, or the like. In some embodiments the primary stabilizers may comprise elastin and collagen, for example, or the like. In some embodiments, the one or more skin penetration enhancers can be selected from the group that includes, for example, d-limonene, allantoin, fulvic acid, myrrh, hydroquinone glyquin, *quillaja saponaria* (QTS), *acanthophyllum squarrosum* (ATS), either singularly or in combination, or the like.

In an embodiment, the *botulinum* toxin composition comprises:
approximately 1 to 40% w/w collagen;
approximately 1 to 40% w/w elastin;
approximately 0.1 to 15% w/w sphingosine phospholipid; and
approximately 0.1 to 15% w/w cerebroside phospholipid.

The composition may also be used for topical administration in a format whereby the composition penetrates the skin and transdermally denervates an underlying muscle.

The composition may include d-limonene to enhance penetration of the active ingredient through the dermal layer. Limonene has been found to be an effective skin penetration enhancer at 0.30%, enhancing skin permeation of *botulinum* toxin Type A approximately fourfold.

*Quillaja saponaria* (QTS) and *Acanthophyllum squarrosum* (ATS) total saponins are two natural skin penetration enhancers that may also be included in the composition. They demonstrate moderate activity as skin penetration enhancers.

Allantoin may also be included in the composition. Allantoin acts as a skin protectant and a mild neutral skin penetration enhancer.

Eldopaque or hydroquinone glyquin may also be included as skin penetration enhancers.

In certain embodiments, the use of collagen in the composition, in combination with elastin and a mixture of sphingosine and cerebroside, maintains the integrity of the complex without denaturing or fragmentation or detoxification. Thus, *botulinum* toxin can be stabilized and the stabilized toxin can be successfully delivered transdermally to achieve similar results to those obtained by intramuscular injection of *botulinum* toxin.

Additional components can be included to formulate the composition into other formats, such as a cream, lotion, spray, mask, gel, etc., that is suitable for topical administration. If formulated as a cream or a solution, the composition should contain the active ingredient in sufficiently concentrated quantities in order that the composition does not drip off the area of administration.

A preferred method for preparing a stabilized *botulinum* toxin composition for topical application below. Briefly, equal amounts of collagen and elastin are solubilized in saline. In a separate flask, equal amounts of sphingosine and cerebroside are dissolved in alcohol. The alcohol is then removed. *Botulinum* toxin A is dissolved in saline and then added to the flask and the flask is swirled to coat the *botulinum* toxin protein with a phospholipid micelle coating. This solution is then added to the solution of collagen and elastin. This method can be used to prepare compositions containing other types of *botulinum* toxin.

The composition may also be provided on a patch that is adhesively secured to the skin so that the active ingredient, such as *botulinum* toxin, can pass from the patch through the skin.

Any feature or combination of features described herein are included within the scope of the present invention provided that the features included in any such combination are not mutually inconsistent as will be apparent from the context, this specification, and the knowledge of one of ordinary skill in the art.

It is known that *botulinum* toxin type A can have an efficacy for up to 12 months (European J. Neurology 6 (Supp 4): S111-S1150:1999), and in some circumstances for as long as 27 months (The Laryngoscope 109:1344-1346: 1999). However, the usual duration of an intramuscular injection of *botulinum* type A is typically about 3 to 4 months.

EXAMPLES

Example 1

A 62 year old man complains of incontinence associated with sexual activity after a radical prostatectomy procedure. Based on a thorough examination, his doctor recommends a course of *botulinum* type A injections to the bladder wall.

The patient is injected with 200 U of *botulinum* type A divided among 30 injections into the bladder wall. Within 7 days of receiving the injections, the patient reports the elimination of the incontinence symptoms.

Example 2

A 41 year old man complains of urinary incontinence at climax. Based on a thorough examination, his doctor recommends *botulinum* type A administration to the bladder wall.

The bladder of the patient is instilled with a solution containing 1000 U of *botulinum* type A by filling the bladder with the solution, allowing the solution to remain within the bladder for 10 minutes, then draining the solution. Within 7 days of receiving the *botulinum* administration, the patient reports the elimination of the incontinence symptoms.

Example 3

A 44 year old man complains of urinary incontinence at penetration after urogenital surgery. Based on a thorough examination, his doctor recommends a series of *botulinum* type A injections to the prostate.

The prostate of the patient is injected with 100 U of *botulinum* at 7-day intervals for 3 weeks. Following the course of injections, the patient's incontinence symptoms are reduced. Specifically, the volume of urine produced at climax is reduced.

Example 4

A 24 year old woman complains of incontinence at penetration. She has previously been diagnosed with detrusor overactivity. Based on a thorough examination, her doctor recommends a series of *botulinum* type A injections to the bladder.

The patient is injected with 400 U of *botulinum* type B divided among 30 injections into the bladder wall. Within 7 days of receiving the injections, the patient reports the elimination of her incontinence symptoms.

Example 5

A 61 year old woman complains of incontinence at climax. She has not been diagnosed with any urological abnormality. Based on a thorough examination, her doctor recommends administration of *botulinum* type A administration to the bladder wall.

The bladder of the patient is instilled with a solution containing 1000 U of *botulinum* type A by filling the bladder with the solution, allowing the solution to remain within the bladder for 10 minutes, then draining the solution. Within 7 days of receiving the *botulinum* administration, the patient reports the elimination of the incontinence symptoms.

Example 6

A 29 year old man complains of urinary incontinence associated with sexual activity after brachytherapy for prostate cancer. Based on a thorough examination, his doctor recommends a course of *botulinum* type A injections to the bladder wall.

The patient is injected with 200 U of *botulinum* type A divided among 30 injections into the bladder wall. Within 7 days of receiving the injections, the patient reports the elimination of the incontinence symptoms.

Example 7

A 55 year old man complains of urinary incontinence associated with sexual activity after radiation therapy for prostate cancer. Based on a thorough examination, his doctor recommends a course of *botulinum* type A injections to the bladder wall.

The patient is injected with 200 U of *botulinum* type A divided among 30 injections into the bladder wall. Within 7 days of receiving the injections, the patient reports the elimination of the incontinence symptoms.

Example 8

A 39 year old man complains of urinary incontinence associated with sexual activity after brachytherapy for prostate cancer. Based on a thorough examination, his doctor recommends a treatment of SUDAFED®.

The patient ingests 2 tablets of SUDAFED® each day. Within 7 days of beginning the treatment, the patient reports the elimination of the incontinence symptoms.

Example 9

A 55 year old man complains of urinary incontinence associated with sexual activity after radiation therapy for prostate cancer. Based on a thorough examination, his doctor recommends a course of *botulinum* type A injections to the bladder wall in combination with a SUDAFED® regimen.

The patient is injected with 200 U of *botulinum* type A divided among 30 injections into the bladder wall. In addition, the patient ingests 2 tablets of SUDAFED® each day. Within 7 days of receiving the injections, the patient reports the elimination of the incontinence symptoms.

Example 10

A 55 year old woman complains of incontinence at climax. She has not been diagnosed with any urological abnormality. Based on a thorough examination, her doctor recommends *botulinum* type A administration to the bladder wall. Based on a thorough examination, her doctor recommends a course of *botulinum* type A injections to the bladder wall in combination with a SUDAFED® regimen.

The patient is injected with 200 U of *botulinum* type A divided among 30 injections into the bladder wall. In addition, the patient ingests 2 tablets of SUDAFED® each day. Within 7 days of receiving the injections, the patient reports the elimination of the incontinence symptoms.

The bladder of the patient is instilled with a solution containing 1000 U of *botulinum* type A by filling the bladder with the solution, allowing the solution to remain within the bladder for 10 minutes, then draining the solution. Within 7 days of receiving the *botulinum* administration, the patient reports the elimination of the incontinence symptoms.

While this invention has been described with respect to various specific examples and embodiments, it is to be understood that the invention is not limited thereto and that it can be variously practiced with the scope of the following claims.

What is claimed is:

1. A method of treating climacturia in a patient in need thereof comprising administering a therapeutically effective amount of a *botulinum* toxin to the bladder of a patient.

2. The method of claim 1, wherein the *botulinum* toxin is administered before, during, after-or combinations thereof, a surgical procedure selected from the group consisting of radical prostatectomy, laparoscopic radical prostatectomy, transurethral resection of the prostate, transurethral microwave therapy, transurethral needle ablation, and cryosurgery.

3. The method of claim 2 wherein the *botulinum* toxin is administered before the surgical procedure.

4. The method of claim 2, wherein the *botulinum* toxin is administered during the surgical procedure.

5. The method of claim 3, wherein the *botulinum* toxin is further administered after the surgical procedure.

6. A method of treating climacturia in a patient previously diagnosed with a urogenic abnormality, comprising administering a therapeutically effective amount of a *botulinum* toxin to a patient in need thereof, thereby treating the climacturia.

7. The method of claim 6, wherein the *botulinum* toxin is selected from the group consisting of types A, B, C, D, E, and, G.

8. The method of claim 1, wherein the *botulinum* toxin is selected from the group consisting of types A, B, C, D, E, and, G.

9. The method of claim 2, wherein the climacturia occurs following the surgical procedure for a prostate disorder.

10. The method of claim 6, wherein the climacturia occurs following the surgical procedure for a prostate disorder.

11. A method of preventing post-surgical climacturia comprising administering a therapeutically effective amount of a *botulinum* toxin to a patient, wherein the *botulinum* toxin is administered prior to the onset of climacturia.

12. The method of claim 11, wherein the *botulinum* toxin is administered before, during or after a surgical procedure.

13. The method of claim 12, wherein the *botulinum* toxin is administered before the surgical procedure.

14. The method of claim 12, wherein the *botulinum* toxin is administered during the surgical procedure.

15. The method of claim 12, wherein the *botulinum* toxin is administered after the surgical procedure.

16. The method of claim 11, wherein the *botulinum* toxin is selected from the group consisting of types A, B, C, D, E, and, G.

17. The method of claim 11, wherein the *botulinum* toxin is administered in a manner selected from the group consisting of topically to the bladder, via injection into the bladder, via injection into the prostate, via implant, and via installation into the bladder.

* * * * *